Oct. 19, 1943. C. S. JONES Plant Pat. 605
CAMELLIA
Filed March 22, 1943
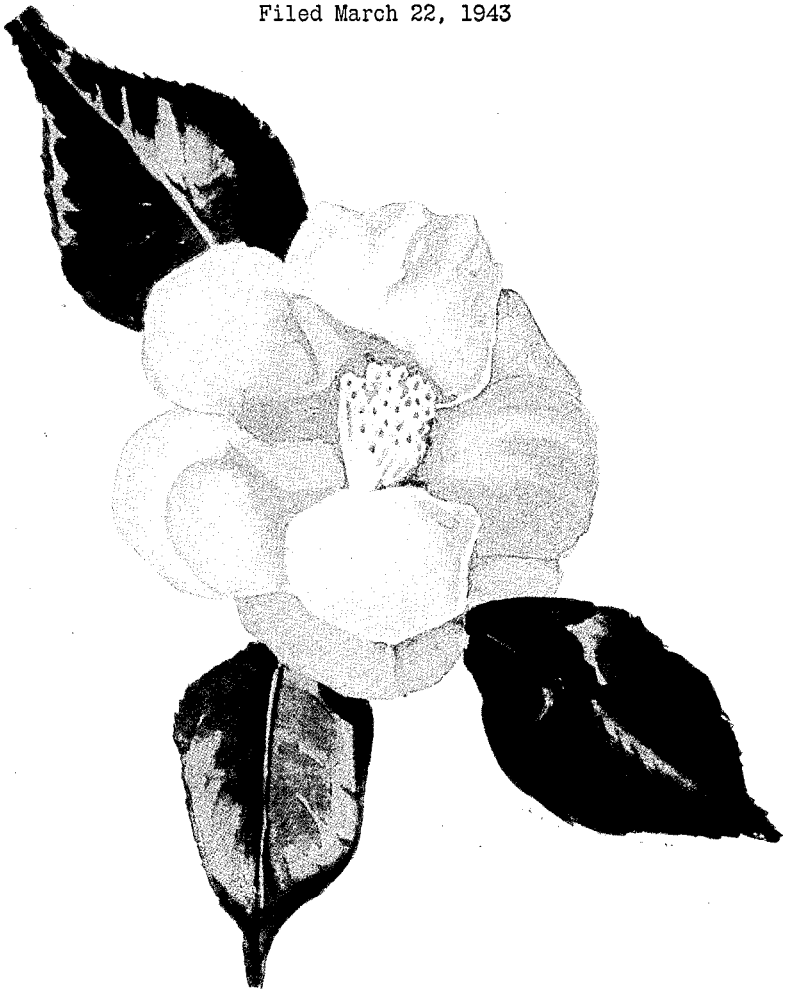
Inventor
Charles S. Jones
By Lyon & Lyon
Attorneys Patented Oct. 19, 1943

Plant Pat. 605

UNITED STATES PATENT OFFICE

605

CAMELLIA

Charles Stone Jones, Pasadena, Calif.

Application March 22, 1943, Serial No. 479,997

1 Claim. (Cl. 47—60)

This invention relates to a new and distinctive variety of camellia which may be generally designated as a semi-double variety, which is almost white at the base, shading to a delicate shell-pink at the outer edges and having a characteristic petal texture of the character which may be compared to the texture of silk crepe de Chine.

The parentage of the camellia is not precisely known, but was produced through cross-pollenization of a seedling camellia. The new and distinctive variety of camellia embracing this invention is characterized by the following characteristics:

1. The texture of the flower petals, which is of crepe characteristics resembling in appearance crepe de Chine, and where the petals are crimped or frizzed, particularly from their outer edges toward the center, the crimping or frizzing being particularly apparent in the inner row of petals.

2. *Color.*—The color of the camellia is characterized in being of a delicate shell-pink at the outer edges of the petals and shading to practically pure white at the base of the stamen on the inner surface of the petals. The colors are comparable with the color plates of the "Dictionary of Color," by A. Maerz and M. Rea Paul, published by McGraw-Hill Book Company, Inc., New York, 1930 edition. The color of the outer petal, at its outer edge, is comparable with, but not exactly the same, as the color indicated on Plate 41, J–1; the color of the petal on the inner row being comparable with that of Plate 41, G–1, and the petal shading toward the base of the stamen of a color comparable with Plate 41, C–1, continuing to shade to practically a pure white at the base of the stamen. The color is further characterized in that in reflected light it has a lavender or orchid shadow.

The stamens, of which there are a large bundle, are pure white at the base and terminate in anthers which carry a profuse quantity of pollen of a golden color comparable, but not exactly the same, as the color of Plate 9, L–7.

The leaves are of a darker green than are common in camellias and are heavily ribbed and veined. The color of the leaf is comparable with that of Plate 23, C–10, the color of the leaf being several shades darker green than the leaf of the common camellia variety known as the "Purity." The leaves are also narrow and longer than the leaf of the "Purity" and are more rangy, that is, of more varying size.

The bush is of the heavy cluster type as distinguished from the long branching characteristics of the common "Purity" variety of camellia. The camellia is further characterized by being of long-lasting quality, that is, the flower when picked has a lasting quality greater than that of the general run of camellias and is of even longer-lasting quality than the common "Purity" camellia, which is among the best in this characteristic.

The camellia is further characterized in that it does not set a multiplicity of buds at the bud terminal, but sets either a single or double bud at the bud terminal and is differentiated from the common characteristic of camellia of setting a mutliplicity of buds at the bud terminals. The camellia is further characterized in the large bud, which is tight, or full ovoid shape and is of pink color in its protruding petals comparable in color, but of a deeper shade, than the color of Plate 41, J–1.

The camellia is further characterized by having a delicate fragrance, which is most pronounced in the newly opening buds but is retained in fully opened flowers.

The flower when fully opened is from 3″ to 4″ in diameter and generally includes two rows of petals, commonly six in number, in each row. The colors and characteristics of this camellia are indicated in the accompanying figure showing the fully opened camellia.

The camellia is further characterized in being of the early blooming type, being one of the first to bloom in the area of Southern California, and blooms very profusely in early December under average weather conditions.

I claim:

The camellia plant variety herein disclosed, characterized by: the flower, with petal texture resembling crepe de Chine, the delicate shell-pink of the petals shading into practically pure white at the base of the stamen, the flower being semi-double, generally including two rows of six petals each, and having a profuse bundle of white stamens; the fragrance herein described, and long-lasting quality as a cut flower; the bushy character of the plant; the dark green, heavily veined leaf structure.

CHARLES STONE JONES.